(12) United States Patent
Retsina et al.

(10) Patent No.: US 8,030,039 B1
(45) Date of Patent: *Oct. 4, 2011

(54) METHOD FOR THE PRODUCTION OF FERMENTABLE SUGARS AND CELLULOSE FROM LIGNOCELLULOSIC MATERIAL

(75) Inventors: Theodora Retsina, Atlanta, GA (US); Vesa Pylkkanen, Atlanta, GA (US)

(73) Assignee: American Process, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/015,007

(22) Filed: Jan. 27, 2011

Related U.S. Application Data

(63) Continuation of application No. 12/250,734, filed on Oct. 14, 2008.

(51) Int. Cl.
*C12P 7/06* (2006.01)
*C12P 7/16* (2006.01)
*C12P 7/02* (2006.01)
*C12P 7/00* (2006.01)
*C12P 1/00* (2006.01)
*D21C 9/08* (2006.01)
*D21C 9/10* (2006.01)
*D21C 3/00* (2006.01)
*D21C 3/04* (2006.01)

(52) U.S. Cl. .......... 435/161; 435/41; 435/132; 435/155; 435/160; 162/1; 162/71; 162/82; 162/83; 162/84

(58) Field of Classification Search ................. 435/161
See application file for complete search history.

(56) References Cited

U.S. PATENT DOCUMENTS

| 2,022,664 | A | 3/1935 | Groombridge et al. |
| 2,060,068 | A | 10/1936 | Groombridge et al. |
| 4,746,401 | A | 5/1988 | Roberts et al. |
| 5,338,405 | A | 8/1994 | Patt et al. |
| 5,705,369 | A | 1/1998 | Torget et al. |
| 6,258,175 | B1 | 7/2001 | Lightner |

OTHER PUBLICATIONS

Pylkkanen, V.A., Characterization of Ethanol-SO2 Pulping and a Preliminary Chemical Recovery Process, M.S. Thesis, 1992 Michigan Technology University, Houghton, MI, USA.*

* cited by examiner

*Primary Examiner* — Sue Liu
*Assistant Examiner* — Sheridan MacAuley
(74) *Attorney, Agent, or Firm* — Altera Law Group, LLC

(57) ABSTRACT

A method for the production of fermentable sugars and high viscosity cellulose from lignocellulosic material in a batch or continuous process is provided. Lignocellulosic material is fractionated in a fashion that cellulose is removed as pulp, cooking chemicals can be reused, lignin is separated for the production of process energy, and hemicelluloses are converted into fermentable sugars, while fermentation inhibitors are removed. High yield production of alcohols or organic acids can be obtained from this method using the final reaction step.

20 Claims, 2 Drawing Sheets

Products from fractionation of lignocellulosic material.

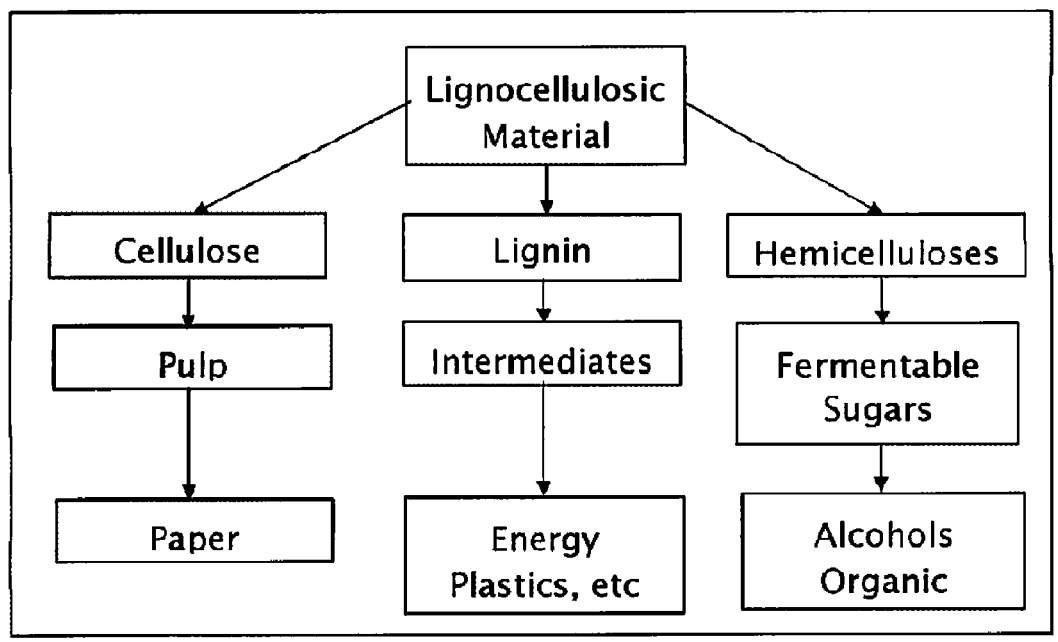
Figure 1 Products from fractionation of lignocellulosic material.

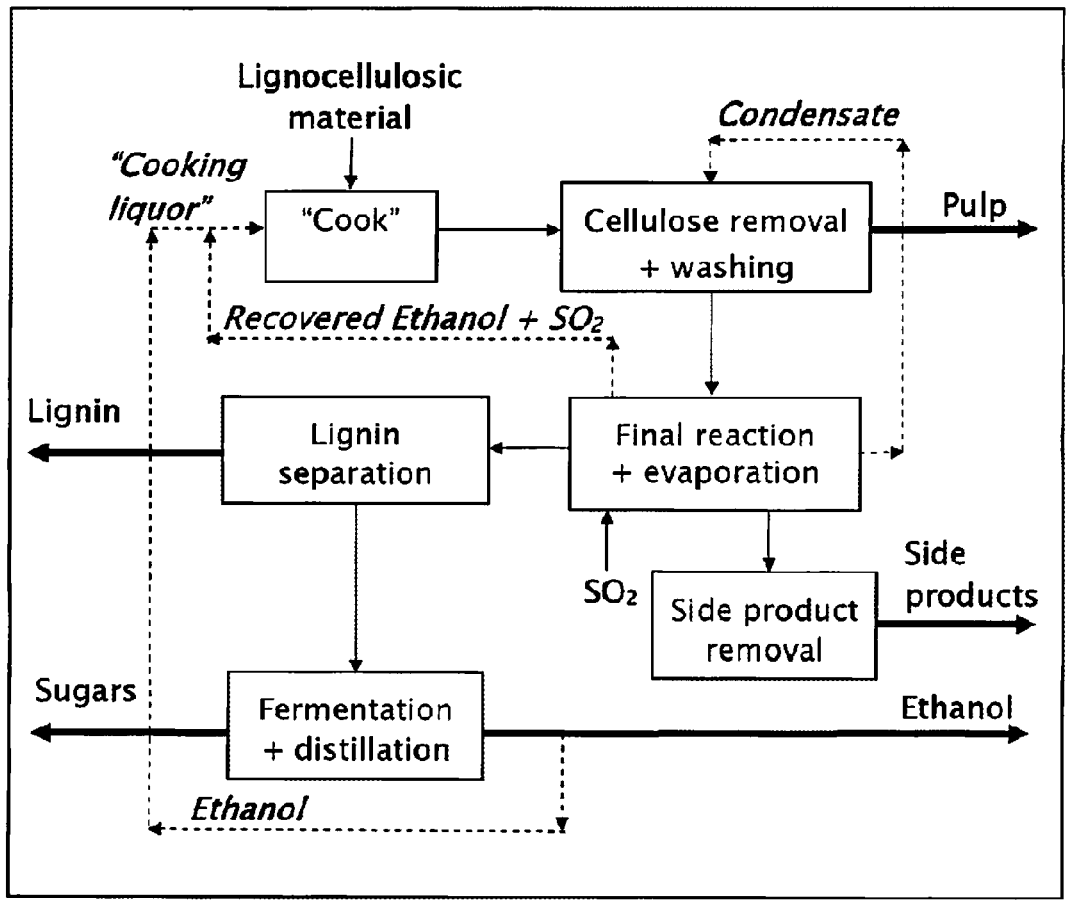
Figure 2. A flow sheet example of the invention process.

METHOD FOR THE PRODUCTION OF FERMENTABLE SUGARS AND CELLULOSE FROM LIGNOCELLULOSIC MATERIAL

CROSS-REFERENCE TO RELATED APPLICATIONS

The present application is a continuation of pending application Ser. No. 12/250,734 filed 14 Oct. 2008, which is a continuation-in-part of application Ser. No. 11/740,923 filed 27 Apr. 2007, now abandoned, which claims the benefit of provisional patent application No. 60/795,487 filed 28 Apr. 2006.

FIELD

This disclosure relates, in general, to the fractionation of lignocellulosic material into lignin, cellulose and hemicelluloses and more particularly to the production of reactive lignin and fermentable sugars while preserving the production of cellulose. The process is integrated to reduce energy consumption and degradation of the products while maintaining flexibility of product yields.

BACKGROUND

Commercial sulfite pulping has been practiced since 1874. The focus of sulfite pulping is the preservation of cellulose. In an effort to do that, industrial variants of sulfite pulping take 6-10 hours to dissolve hemicelluloses and lignin producing a low yield of fermentable sugars.
Stronger acidic cooking conditions that hydrolyze the hemicelluloses to produce a high yield of fermentable sugars also hydrolyze the cellulose and therefore the cellulose is not preserved.

Sulfite pulping produces spent cooking liquor termed sulfite liquor. Fermentation of sulfite liquor to hemicellulosic ethanol has been practiced primarily to reduce the environmental impact of the discharges from sulfite mills since 1909. Published design data from one of the two known remaining sulfite mills that produces ethanol, shows ethanol yields not to exceed 33% of original hemicelluloses. Ethanol yield is low due to the incomplete hydrolysis of the hemicelluloses to fermentable sugars and further compounded by sulfite pulping side products, such as furfural, methanol, acetic acid and others, inhibiting fermentation to ethanol.

Energy use for ethanol production in said sulfite mill applications is higher than the energy value of the ethanol produced. Furthermore, this sulfite process uses calcium sulfite or ammonium sulfite and has no chemical recovery, therefore chemical losses are high. Because of poor ethanol yield, lower cost of synthetic ethanol production, and the production of ethanol from corn today, only two sulfite mills are known to have continued the practice of hemicellulosic ethanol production to date.

In the $20^{th}$ century, Kraft pulping eclipsed sulfite pulping as the dominant chemical pulping method.

Kraft pulping however does not hydrolyze the hemicelluloses into fermentable sugars; instead hemicelluloses are in solution with soluble inorganic cooking chemicals and cannot readily be separated.

The number of sulfite pulp mills remaining in operation continues to reduce each year. The main reasons are that when compared to Kraft pulping, sulfite pulping produces inferior strength pulp, requires more cooking time, requires aged wood as the raw material (green wood cannot be readily used), is not feasible on as many different wood species, and lacks an efficient method of chemical recovery therefore chemical losses are high.

Other processes using solvent cooking chemicals have been tried as an alternative to Kraft or sulfite pulping. Original solvent processes are described in the U.S. Pat. No. 1,856,567 to Kleinert et al. and U.S. Pat. No. 2,060,068 to Groombridge et al. Although three demonstration size facilities for ethanol-water (ALCELL), alkaline sulfite with anthraquinone and methanol (ASAM), and ethanol-water-sodium hydroxide (Organocell) were operated briefly in the 1990's, today there are no full scale solvent pulping mills. None of these solvent processes provided for fermentable sugar production from hemicelluloses.

Groombridge shows that an aqueous solvent with sulfur dioxide is a potent delignifying system to produce cellulose from lignocellulosic material.

Furthermore, U.S. Pat. No. 5,879,463 to Proenca reveals that simultaneous delignification and rapid hydrolysis of the entire cellulosic material, both the cellulose and the hemicelluloses, is possible in the presence of an organic solvent and a dilute inorganic acid; however this process does not preserve the cellulose.

Therefore in the prior art of processing lignocellulosic material for the primary purpose of producing cellulose:
a) The sulfite processes to date (including base sulfite and ethanol sulfite) in an effort to preserve the cellulose, do not yield complete hydrolysis of hemicelluloses and produce fermentation inhibitors, thereby resulting in low yields of fermentable sugars in the sulfite liquor and furthermore, low yield of any downstream fermentation products from said sugars.
b) Strong acid processing of lignocellulosic material degrades and hydrolyzes both hemicelluloses and cellulose, therefore cellulose is not preserved.
c) The Kraft process does not hydrolyze hemicelluloses to fermentable sugars.
d) Organic solvent pulping methods did not hydrolyze hemicelluloses to fermentable sugars, i.e., only part were hydrolyzed, not all.
e) Treatment of lignocellulosic material with dilute inorganic acid in organic solvent hydrolyzes both cellulose and hemicelluloses and therefore does not preserve the cellulose.
f) In the Kraft process lignin condensation causes loss of lignin reactivity.

BRIEF SUMMARY

This summary is provided only for the purpose of aiding the reader in understanding the full disclosure which follows below. It does not provide the scope of the invention. That is to be found in the claims.

The present disclosure describes a process for the production of fermentable sugars by fractionating lignocellulosic material into lignin, cellulose and hydrolyzed hemicelluloses through a staged treatment of the lignocellulosic material with a solution of aliphatic alcohol, water and sulfur dioxide, in a one, two or multiple step process with or without alkaline additive where the cellulose and reactive native lignin are removed and preserved in an intermediary step, the hemicelluloses are converted to fermentable sugars, and fermentation inhibitors are removed. Hence in a preferred embodiment lignocellulosic material is treated in a first stage with aliphatic alcohol, water and sulfur dioxide, the cellulose is then removed, and then a further treatment of the material is conducted with heat and sulfur dioxide.

The present inventors have now developed a method wherein the hemicelluloses of a lignocellulosic material can be converted to fermentable sugars while preserving the cellulose. A high yield of fermentable sugars can be obtained together with a cellulose product. Further it has been shown that the spent cooking liquor, termed hydrolyzate, produced according to the method of present disclosure can be used to produce high yields of ethanol. Surprisingly, ethanol production using hydrolyzate from the method of the present disclosure was 2.5 times higher than when using hydrolyzate that was not from the method of the present disclosure. This has been achieved through cooking lignocellulosic material with sulfur dioxide in a solution of ethanol and water in a one or multiple stage process where cooking is continued after intermediary removal of the cellulose. This can be done in a batch process with a cycle time of between 0.5 and 6 hours, or in a continuous process.

Surprisingly, an addition of small amounts of ammonia to the alcohol sulfite pulping liquor resulted in significant improvement in cellulose viscosity, higher yield and brightness and comparable residual lignin content. The ammonia is not recovered with volatile cooking chemicals. Instead ammonia compounds remains in the liquor through the fermentation of the liquor and acts as nutrients providing nitrogen to the micro-organisms. The residual ammonium sulfite is circulated back to the pulp washing. The present inventors have now developed a process for the treatment of lignocellulosic material which produces strong pulp, fractionates the material and then converts each fraction into a reactive chemical feedstock.

The following are other aspects of the disclosure.

There is disclosed a process for producing fermentable sugars from hemicelluloses of a lignocellulosic material through a staged treatment of the lignocellulosic material with a solution of aliphatic alcohol, water and sulfur dioxide with intermediate removal and preservation of cellulose.

Also disclosed is a process wherein said solution of aliphatic alcohol, water and sulfur dioxide contains 40% to 60% water.

Also disclosed is a process wherein a different concentration of said solution of aliphatic alcohol, water and sulfur dioxide is used at a first stage of treatment of said lignocellulosic material than is used in one or more subsequent stages of treatment with intermediate removal and preservation of cellulose.

Also disclosed is a process wherein a sulfur dioxide solution of 3% to 9% is used at a first stage of treatment and a sulfur dioxide, sulfurous acid or sulfuric acid solution of 0.05% to 9% is used in one or more subsequent stages of treatment with intermediate removal and preservation of cellulose.

Also disclosed is a process wherein said process is followed by steam stripping and/or evaporation of the hydrolyzate to remove and recover sulfur dioxide and alcohol and to remove fermentation inhibitors.

Also disclosed is a process wherein a sulfur dioxide solution of 0.05% to 3% is used at a first stage of treatment and a sulfur dioxide, sulfurous acid or sulfuric acid solution of 0.05% to 9% is used in one or more subsequent stages of treatment with intermediate removal and preservation of cellulose.

Also disclosed is a process wherein said process is followed by steam stripping and/or evaporation of the hydrolyzate to remove and recover sulfur dioxide and alcohol and to remove fermentation inhibitors.

Also disclosed is a process wherein said process is carried out at temperatures between 65° C. and 200° C.

Also disclosed is a process wherein said process is carried out at for a period of time between 15 minutes and 360 minutes.

Also disclosed is a process wherein preferred conditions are an initial treatment using 48% ethanol, 48% water and 4% sulfur dioxide at 140° C. for 2 hours, and following the intermediate removal and preservation of the cellulose, a final treatment 48.5% ethanol, 48.5% water and 3% sulfur dioxide at 140° C. for 1 hour.

Also disclosed is a process for producing fermentable sugars from the hemicelluloses of a lignocellulosic material through a staged treatment of the lignocellulosic material with a solution of aliphatic alcohol, water and sulfur dioxide with intermediate removal of hydrolyzate and preservation of the cellulose.

Also disclosed is a process wherein a different concentration of said solution of aliphatic alcohol, water and sulfur dioxide is used at a first stage of treatment of said lignocellulosic material than is used in one or more subsequent stages of treatment with intermediate removal of hydrolyzate and preservation of the cellulose.

Also disclosed is a process wherein said process is carried out at for a period of time between 15 minutes and 360 minutes.

Also disclosed is a process wherein aliphatic alcohol is produced from fermenting and distilling the hydrolyzed fermentable sugars produced in said process and is then reused in said process.

Also disclosed is a process wherein lignin is sulfonated and rendered soluble in aqueous solutions.

Also disclosed is a process wherein the concentration of sulfur dioxide and aliphatic alcohol in the solution and the time of cook is varied to control the yield of hemicelluloses vs. celluloses and vs. fermentable sugars.

Also disclosed is a process for producing hemicellulosic ethanol from lignocellulosic material through a staged treatment of the lignocellulosic material with a solution of aliphatic alcohol, water and sulfur dioxide comprising the steps of:

Cooking under acidic conditions to produce hydrolyzed hemicelluloses, cellulose, and sulfonated lignin;

Washing to separate lignin and hemicelluloses from cellulose in several stages to recover over 95% of the aliphatic alcohol mixed with the cellulose;

Treatment of post washing hydrolyzate with sulfur dioxide and heat to maximize the yield of fermentable sugars and to remove, and/or neutralize fermentation inhibitors;

Evaporation to remove and recover cooking chemicals, remove side products and concentrate lignin and/or fermentable sugars product;

Lignin separation to remove lignin and lignosulfonates from fermentable sugars

Fermentation and distillation to produce and concentrate alcohols or organic acids; and Fractionation and/or separation to remove and recover side products.

Also disclosed is a process for producing hemicellulosic ethanol comprising the steps of:

Producing fermentable sugars according to the process of Claim 1; and

Subjecting the hydrolyzate to evaporation to remove and recover cooking chemicals and/or remove side products and/or concentrate lignin and/or concentrate hemicellusoses product.

Also disclosed is a process further comprising the step of fractionation and/or separation to remove and recover side products.

Also disclosed is a process further comprising the step of lignin and/or lignosulfonate separation.

Also disclosed is a process further comprising the step of fermentation and distillation.

Also disclosed is a process wherein a sulfur dioxide solution of 9% to 20% is used.

Also disclosed is a process wherein a sulfur dioxide solution of 20% to 30% is used.

Also disclosed is a process wherein an additive is used in a solution of aliphatic alcohol, water and sulfur dioxide at a first stage of treatment of said lignocellulosic material.

Also disclosed is a process wherein the additive is ammonium hydroxide in amounts 0.01 to 10% in the solution.

Also disclosed is a process wherein the additive is anthraquinone in amounts 0.001 to 1% in the solution.

Also disclosed is a process wherein the additive is magnesium hydroxide in amounts 0.01 to 10% in the solution.

Also disclosed is a process wherein the additive is urea in amounts 0.01 to 10% in the solution.

Also disclosed is a process wherein the additive is sodium hydroxide in amounts 0.01 to 10% in the solution.

Also disclosed is a process, wherein aliphatic alcohol soluble lignin is separated from hydrolyzate by evaporation of said aliphatic alcohol and subsequent removal of reactive native lignin precipitate.

Also disclosed is a process where reactive lignosulfonates are selectively precipitated from hydrolyzate using excess lime in the presence of aliphatic alcohol.

Also disclosed is a process wherein the concentration of sulfur dioxide, additives, and aliphatic alcohol in the solution and the time of cook is varied to control the yield of cellulose and hemicelluloses in pulp.

Also disclosed is a process wherein the concentration of sulfur dioxide, and the time of cook is varied to control the yield of lignin versus lignosulfonates in the hydrolyzate.

Also disclosed is a process wherein the concentration of sulfur dioxide, temperature and the time of cook is varied to control the yield of hemicelluloses versus fermentable sugars.

Also disclosed is a process wherein hydrated lime is used to precipitate lignosulfonates.

Also disclosed is a process, wherein the cooking step may be in liquid or vapor phase conditions.

Also disclosed is a process, wherein evaporated vapor streams are segregated so as to have different concentrations of organic compounds in different streams.

Also disclosed is a process, wherein evaporator condensate streams are segregated so as to have different concentrations of organic compounds in different streams.

Also disclosed is a process wherein distillation column bottoms solution and evaporator condensate are reused to wash cellulose.

Also disclosed is a process wherein the hydrolyzate is subjected to autohydrolyzate by heating under pressure.

Also disclosed is a process wherein said process is carried out at for a period of time between 360 minutes and 720 minutes.

Also disclosed is a process wherein part of the lignin is precipitated in reactive native form and the remaining lignin is sulfonated in water soluble form.

Also disclosed is a process wherein the evaporation process may be under vacuum or pressure from −0.1 atmospheres to 6.0 atmospheres Also disclosed is a process wherein the evaporation process comprises an integrated alcohol stripper and evaporator.

BRIEF DESCRIPTION OF THE DRAWINGS

A more complete understanding of the present disclosure may be obtained by reference to the following detailed description when read in conjunction with the accompanying drawings wherein:

FIG. 1. Illustrates the products obtained from the fractionation of lignocellulosic material.

FIG. 2. Illustrates a flow sheet example of one process, noting that the process steps may be in other sequences.

DETAILED DESCRIPTION

The first process step is "cooking" which fractionates the three lignocellulosic material components to allow easy downstream removal; specifically hemicelluloses are dissolved and over 50% are completely hydrolyzed, cellulose is separated but remains resistant to hydrolysis, and lignin is sulfonated in water soluble form. Lignocellulosic material is processed, "cooked", in a solution of aliphatic alcohol, water, and sulfur dioxide where typical ratios by weight are 40-60% of both aliphatic alcohol and water, and 0.05-9% of sulfur dioxide, and preferably 50% aliphatic alcohol, 50% water, and 0.05-9% sulfur dioxide; this solution is termed cooking liquor. Aliphatic alcohols can include ethanol, methanol, propanol and butanol, but preferably ethanol. The cooking is performed in one or more stages using batch or continuous digesters. Depending on the lignocellulosic material to be processed, the cooking conditions are varied, with temperatures from 65° C. to 170° C., for example 65° C., 75° C., 85° C., 95° C., 105° C., 115° C., 125° C., 130° C. 135° C., 140° C., 145° C., 150° C., 155° C., 165° C. or 170° C., and corresponding pressures from 1 atmosphere to 15 atmospheres. The sulfur dioxide charge in the cooking liquor is varied between 0.05% and 9%, for example 0.05%, 0.1%, 0.5%, 1%, 2%, 2.5%, 3%, 3.5%, 4%, 5%, 6%, 7%, 8% or 9%, of the total cooking liquor mass in one or more cooking stages. Cooking time of each stage is also varied between 15 minutes and 360 minutes, for example 15, 30, 45, 60, 90, 120, 140, 160, 180, 210, 240, 270, 300, 330 or 360 minutes. The lignocellulosic material to cooking liquor ratio can is varied between 1:3 to 1:6, for example, 1:3, 1:4, 1:5 or 1:6, and preferably 1:4. In an alternative embodiment part of this cooking step the lignin is precipitated in reactive native form and the remaining lignin is sulfonated in water soluble form, the cooking is performed in one or more stages using batch or continuous digesters, and in liquid or vapor phase conditions, with temperatures from 65° C. to 170° C., the sulfur dioxide charge in the cooking medium is varied between 0.05% and 30%, cooking time is varied between 15 and 720 minutes and the lignocellulosic material to cooking liquor ratio is varied between 1:3 to 1:6. In all embodiments an additive may be included in amounts of 0.1% to 10% or more to increase cellulose viscosity. The additives include ammonia, ammonia hydroxide, urea, anthraquinone, magnesium oxide, magnesium hydroxide, sodium hydroxide, and their derivatives. In all embodiments the concentration of sulfur dioxide, additives, and aliphatic alcohol in the solution and the time of cook is varied to control the yield of cellulose and hemicelluloses in pulp. In all embodiments the concentration of sulfur dioxide, and the time of cook is varied to control the yield of lignin versus lignosulfonates in the hydrolyzate. In all embodiments the concentration of sulfur dioxide, temperature and the time of cook is varied to control the yield of hemicelluloses versus fermentable sugars.

Hydrolyzate from the cooking step is subjected to pressure reduction, either at the end of a cook in a batch digester, or in an external flash tank after extraction from a continuous digester. The flash vapor from the pressure reduction is collected into a cooking liquor make-up vessel. The flash vapor contains substantially all the unreacted sulfur dioxide which is directly dissolved into new cooking liquor. The cellulose is then removed to be washed and further treated as required.

The process washing step recovers the hydrolyzate from the cellulose. The washed cellulose is pulp that can be used for paper production or other purposes. The weak hydrolyzate from the washer continues to the final reaction step; in a continuous digester application this weak hydrolyzate will be combined with the extracted hydrolyzate from the external flash tank. The washed cellulose can also be used for ethanol manufacture.

In the final reaction step, the hydrolyzate is further treated in one or multiple steps with a solution of aliphatic alcohol, water, and sulfur dioxide, sulfurous acid or sulfuric acid, where typical ratios by weight are 40-60% of both aliphatic alcohol and water, and sulfur dioxide, sulfurous acid or sulfuric acid to a charge of 0.05% and 9%, for example 0.05%, 0.1%, 0.5%, 1%, 2%, 2.5%, 3%, 3.5%, 4%, 5%, 6%, 7%, 8% or 9%, and directly or indirectly heated to temperatures up to 200° C., for example 105° C., 115° C., 125° C., 135° C., 140° C., 145° C., 150° C., 155° C., 160° C. 170° C., 180° C. 190° C. or 200° C., and preferably 140° C. Said solution may or may not contain residual alcohol. The final reaction step produces fermentable sugars which can then be concentrated by evaporation to a fermentation feedstock. Concentration by evaporation can be before or after the treatment with sulfur dioxide, sulfurous or sulfuric acid in said final reaction step. The final reaction step may or may not be followed by steam stripping of the resultant hydrolyzate to remove and recover sulfur dioxide and alcohol and for removal of potential fermentation inhibiting side products. The evaporation process may be under vacuum or pressure from −0.1 atmospheres to 3.0 atmospheres, for example 0.1, 0.3, 0.5, 1.0, 1.5, 2.0, 2.5, or 3.0 atmospheres.

Alcohol is recovered from the evaporation process by condensing the exhaust vapor and is returned to the cooking liquor make-up vessel in the cooking step. Clean condensate from the evaporation process is used in the washing step. The hydrolyzate from the evaporation and final reaction step contains mainly fermentable sugars but may also contain lignin depending on the location of the lignin separation step in the overall process configuration, and is concentrated between 10% and 55% solids, for example 10%, 15%, 20%, 25%, 30%, 35%, 40%, 45%, 50% or 55%; this hydrolyzate continues to a subsequent process step. In an alternate embodiment of this final reaction step the hydrolyzate is further treated in one or multiple steps by heating with or without adding sulfur dioxide, sulfurous acid or sulfuric acid, to a charge of between 0.05% and 30%. In an alternate embodiment the evaporation process may be under vacuum or pressure from −0.1 atmospheres to 6.0 atmospheres. In an alternate embodiment the hydrolyzate is subjected to autohydrolyzate by heating under pressure. In a preferred embodiment the evaporation step comprises an integrated alcohol stripper and evaporator. In all embodiments evaporated vapor streams are segregated so as to have different concentrations of organic compounds in different streams. In all embodiments evaporator condensate streams are segregated so as to have different concentrations of organic compounds in different streams.

Fermentable sugars are defined as hydrolysis products of cellulose, galactoglucomannan, glucomannan, arabinoglucuronoxylans, arabinogalactan, and glucuronoxylans in to their respective short-chained oligomers and monomer products, i.e., glucose, mannose, galactose, xylose, and arabinose, which are substantially free of fermentation inhibitors. In a preferred embodiment, this is a solution of monomer sugars essentially free of fermentation inhibitors. In a most preferred embodiment it is a solution of monomer sugars with concentration of furfural below 0.15% of the sugars.

The process lignin separation step is for the separation of lignin from the hydrolyzate and can be located before or after the final reaction step and evaporation. If located after, then lignin precipitates from the hydrolyzate since alcohol has been removed in the evaporation step. The remaining water soluble lignosulfonates are precipitated by converting the hydrolyzate to an alkaline condition using an alkaline earth oxide, preferably calcium oxide. The combined lignin and lignosulfonate precipitate is filtered. The lignin and lignosulfonate filter cake can be dried as a saleable byproduct or be burned or gasified for energy production. The hydrolyzate from filtering can be either be sold as a concentrated sugar solution product or be further processed in a subsequent fermentation step. Calcium oxide is commonly known as lime. In an alternate embodiment, if located after, then aliphatic alcohol soluble lignin precipitates from the hydrolyzate since alcohol has been removed in the evaporation step. In an alternate embodiment reactive lignosulfonates are selectively precipitated from hydrolyzate using excess lime in the presence of aliphatic alcohol. In an alternate embodiment hydrated lime is used to precipitate lignosulfonates.

The process fermentation and distillation step is for the production of alcohols, most preferably ethanol, or organic acids. After removal of cooking chemicals and lignin, and treatment in the final reaction step, the hydrolyzate contains mainly fermentable sugars in water solution from which any fermentation inhibitors have been removed or neutralized. The hydrolyzate is fermented to produce dilute alcohol or organic acids, from 1% to 10% concentration. The dilute alcohol is distilled to concentrate to near to its azeotropic point of 95-96% by weight. Some of the alcohol produced from this stage is used for the cooking liquor makeup in the process cooking step. The majority of the alcohol produced is excess and is purified for saleable grade product. In an alternate embodiment distillation column bottoms solution, with or without evaporator condensate, are reused to wash cellulose. In an alternate embodiment lime may be used also to dehydrate product alcohol.

The process side products removal step uses fractionation or separation techniques to remove side products from the hydrolyzate that are of economic value or accumulate to inhibit the yield and quality of the alcohol or pulp products. These side products are isolated by processing the vent from the final reaction step and the condensate from the evaporation step. Side products include furfural, methanol, and acetic acid.

Although other modifications and changes may be suggested by those skilled in the art, it is the intention of the inventors to embody within the patent warranted hereon all changes and modifications as reasonably and properly come within the scope of their contribution to the art.

Example 1

The following example illustrates an aspect of the disclosure but in no way limits it:—

Wood chips of mixed northern pine species, containing 42.68% moisture, were cooked for 180 minutes at 157° C. in a 1 liter Parr reactor. The moisture adjusted cooking liquor consisted of 3% SO2, 48.5% of ethanol and 48.5% water by weight in 6 parts of total liquor to 1 part of dry wood.

Cellulose was removed representing 37.1% of the original wood mass.

The monomer sugars represented 61% of the all sugars in the hydrolyzate as determined by autoclaving the hydrolyzate with 4% $H_2SO_4$ in 121° C. for 60 minutes, which converted the remaining sugars in their corresponding monomers.

Half of the hydrolyzate was processed without the final reaction step. Calcium oxide was added to reach pH of 11 in the hydrolyzate and the precipitate containing calcium lignosulfonates was filtered off. The cooking ethanol was distilled off until the boiling point of the distillate reached 100.5° C. and density of 0.995 g/mL. The furfural content was determined to be 0.29 g/L in the untreated hydrolyzate after the lignin removal and evaporation step.

The second half of the hydrolyzate was subjected to the final reaction step by injecting 3% by weight of sulfur dioxide and heating for 30 minutes at 140° C. Calcium oxide was added to reach pH of 11 in the hydrolyzate and the precipitate containing calcium lignosulfonates was filtered off. The cooking ethanol was distilled off until the boiling point of the distillate reached 100.5° C. and density of 0.995 g/mL. The furfural content was determined to be 0.06 g/L in the hydrolyzate after the final processing step.

The untreated hydrolyzate, i.e., that was not subjected to the final reaction step, and the treated hydrolyzate, i.e., that was subjected to the final reaction step, were both prepared for fermentation by neutralizing with acetic acid, adding sodium citrate and commercial nutrient broth. Initial sugar composition and subsequent hydrolyzate composition were determined in HPLC.

Fermentation of both hydrolyzates was performed in a laboratory setting using *saccharomyces cerevisiae* yeast for at least 72 hours at 35° C.

The yield of ethanol from the untreated hydrolyzate corresponded to only 18.6% stoichiometric yield of the original oligomer sugars and monomer sugars present in the hydrolyzate.

TABLE 1

Monomer sugar concentration of the hydrolyzate and the product ethanol concentration as a function of fermentation time for the untreated hydrolyzate

| Fermentation Time (hours) | Glucose Conc. (g/L) | Xylose Conc. (g/L) | Galactose Conc. (g/L) | Arabinose Conc. (g/L) | Mannose Conc. (g/L) | Total Sugars Conc. (g/L) | Ethanol Conc. (g/L) |
|---|---|---|---|---|---|---|---|
| 0 | 9.33 | 11.83 | 5.30 | 1.94 | 12.05 | 40.45 | 0.00 |
| 24 | 7.55 | 13.91 | 6.17 | 1.69 | 13.22 | 42.54 | 3.76 |
| 48 | 5.85 | 14.79 | 6.71 | 1.84 | 13.48 | 42.67 | 5.57 |
| 72 | 4.41 | 14.74 | 6.68 | 1.74 | 12.72 | 40.29 | 6.30 |

The yield of ethanol from the hydrolyzate treated in the final processing step corresponded to 46.5% stoichiometric yield of the original monomer and oligomer sugars in the hydrolyzate, or 2.5 times greater than the amount from the untreated hydrolyzate.

TABLE 2

Monomer sugar concentration of the hydrolyzate and the product ethanol concentration as a function of fermentation time for the hydrolyzate treated in the final reaction step.

| Fermentation Time (hours) | Glucose Conc. (g/L) | Xylose Conc. (g/L) | Galactose Conc. (g/L) | Arabinose Conc. (g/L) | Mannose Conc. (g/L) | Total Sugars Conc. (g/L) | Ethanol Conc. (g/L) |
|---|---|---|---|---|---|---|---|
| 0 | 8.85 | 10.34 | 4.63 | 1.77 | 10.99 | 36.58 | 0.00 |
| 24 | 4.31 | 9.23 | 4.13 | 1.19 | 8.81 | 27.67 | 3.53 |
| 48 | 0.99 | 9.79 | 4.47 | 1.22 | 7.24 | 23.71 | 7.05 |
| 72 | 0.00 | 6.76 | 3.22 | 1.89 | 3.05 | 14.22 | 14.21 |

Example 2

The following example illustrates one embodiment for producing the advantages of producing stronger pulp in ammonia, ethanol water and sulfur dioxide from softwood, but in no way limits it:—

200 oven dry grams of Red pine wood chips containing 10.5% moisture were screened between ½" and 2" sieves. The moisture adjusted cooking liquor was prepared consisting of 15% $SO_2$, 42.5% of ethanol and 42.5% water by weight in 6 parts of total liquor to 1 part of dry wood by weight. A 2-liter Parr reactor contents were heated up to 150° C. and held for ten minutes at the temperature.

Pulp was washed with 50 vol-% aqueous ethanol and defiberized in a mixer to represent 47.2% of the original wood mass. The screening of the pulp produced 0.8% of rejects on original wood. The lignin free pulp yield was 45.0% as calculate from Kappa number of 30.5. Therefore, the final screened lignin free pulp yield was 44.2%. The intrinsic viscosity was measured using TAPPI standard procedure to 862 ml/g.

When the experiment was repeated under the same conditions, except ammonium hydroxide was added reach 0.1 M concentration, the total yield increased to 56.2%. However, the screen rejects were 8.2% at Kappa number of 63.9. Therefore, the screened lignin free pulp yield was 43.3%.

Two more experiments were performed by increasing the cooking time at the temperature to 20 minutes and 30 minutes. The screened lignin free pulp yield increased to 46.2% and 46.1%, respectively. Moreover, the intrinsic viscosity remained above 1000 ml/g or 32% and 16% higher than without ammonia addition.

TABLE 3

Results from cooking Pine in ethanol, water, and sulfur dioxide medium without and with ammonium addition.

| Cooking time at temperature | Ammonia Molarity | Pulp yield (% wood) | Rejects (% wood) | Kappa | Viscosity (ml/g) |
|---|---|---|---|---|---|
| 10 min | 0 | 47.2 | 0.79 | 30.5 | 862.3 |
| 10 min | 0.1 M | 56.2 | 8.15 | 63.9 | 1321.3 |
| 20 min | 0.1 M | 61.0 | 2.00 | 37.4 | 1140.1 |
| 30 min | 0.1 M | 47.6 | 0.15 | 17.4 | 1001.9 |

Example 3

The following example illustrates one embodiment but in no way limits it:—

Several batches of green southern pine wood chips were cooked in a lab digester with nominal capacity of 10 liter at or below 150° C. for less than one hour. The moisture adjusted cooking liquor consisted of 12-18% SO2 by weight dissolved in 50/50 of ethanol water mixture. The liquor volume was approximately 6 parts of total liquor to 1 part of dry wood. Cellulose was removed after pulping representing 45-50% of the original wood mass. The wash water was mixed and evaporated in a rotary vacuum evaporator at 45-90° C., until liquor volume the ethanol undetectable. The resulting hydrolyzate, containing approximately was cooled in the cold room (4° C.) to room. No settling of suspended solids was observed after several days. The liquor was subjected to three treatments.

First portion (01) of the liquor was adjusted to pH 1 using concentrated sulfuric acid. The liquor was heated to 120° C. for one hour. Precipitate was observed.

Second portion (02) of the liquor was adjusted to pH 1 using concentrated sulfuric acid. The liquor was heated to 90° C. for 10 minutes. Precipitate was observed.

Third portion (03) of the liquor had no sulfuric acid treatment after the evaporation, but it was heated to 90° C. for 10 minutes. Precipitate was observed.

All precipitates were filtered and washed with distilled water until pH 4 was reached. Filter cakes were air dried and sent for elemental analysis and the results are shown in the table below.

TABLE 4

Lignin analysis results.

| SAMPLE ID | 01 | 02 | 03 |
|---|---|---|---|
| Carbon % | 62.43 | 62.38 | 65.71 |
| Hydrogen % | 6.10 | 6.24 | 7.35 |
| Nitrogen % | 0.17 | 0.17 | 0.24 |
| Oxygen (Merz) % | 30.94 | 30.90 | 24.93 |
| Sulfur % | 1.63 | 1.65 | 1.92 |
| HHV BTU/lb | 11158. | 11187. | 12585. |

The table 4 shows that the sample without sulfuric acid treatment retained high carbon to oxygen ratio. This is indication of no or little reaction during the treatment. The high heating value was similar to lignin obtained by centrifuging only. Sulfuric acid appear to react with lignin and thus lower its reactivity.

Example 4

The remaining filtrate after lignin filter cake from example 3 was analyzed for monomeric sugar content using high pressure liquid chromatography (Sample no. 1). The filtrate was first evaporated in rotovap to remove distilled water added during the lignin separation. The pH value of the evaporated liquor was lower than 1.0, usually between 0.93 and 0.98. Then, the hydrolyzate was subjected to secondary hydrolysis to establish maximum yield of monosugars by using standard conditions with adding concentrated sulfuric acid to get 4% solution and then heating solution in Parr reactor at 120° C. for 1 hour (Sample no. 3). This experiment was repeated without adding sulfuric acid and heated in Parr reactor at 120° C. for 1 hour and 2 hours (Sample no. 2). The secondary hydrolysis was analyzed in HPLC and the sugar content is shown in table 5.

TABLE 5

The monosugar content of the hydrolyzate before secondary hydrolysis (1), after hydrolysis with heat treatment only (2), and after 4% sulfuric hydrolysis (3).

| Sample no. | pH value before hydrolysis | pH value after hydrolysis | Glucose (mg/ml) | Xylose (mg/ml) | Galactose (mg/ml) | Arabinose (mg/ml) | Mannose (mg/ml) | Sum of monosugars (mg/ml) |
|---|---|---|---|---|---|---|---|---|
| 1 | 0.98 | — | 4.25 | 11.81 | 6.84 | 3.73 | 13.36 | 39.99 |
| 2 | 0.98 | 0.97 | 7.00 | 13.29 | 6.94 | 4.96 | 21.60 | 53.79 |
| 3 | 0.47 | 0.50 | 6.71 | 11.26 | 6.25 | 4.36 | 25.32 | 53.90 |

This experiment shows that the hydrolyzate is capable of autohydrolysis upon heating the liquor without use of sulfuric acid.

What is claimed is:
1. A process for producing fermentable hemicellulose sugars from a lignocellulosic material, said process comprising:
  (a) contacting a lignocellulosic material with a first solution of an aliphatic alcohol, water, and a first amount of sulfur dioxide in a first stage to produce a first mixture comprising cellulose, hemicellulose oligomers, lignin, and lignosulfonates, wherein said first amount of sulfur dioxide is in a moisture-adjusted concentration of from 12 wt % to 30 wt % in said first solution within said first stage;
  (b) removing and recovering cellulose pulp from said first mixture, to produce a second mixture comprising hemicellulose oligomers, lignin, and lignosulfonates;
  (c) contacting said second mixture with a second amount of sulfur dioxide in a second stage, in the presence of heat, to further hydrolyze said hemicellulose oligomers into fermentable hemicellulose sugars, wherein said second amount of sulfur dioxide is in a concentration of from 0.05 wt % to 9 wt % in a second solution within said second stage;
  (d) removing at least a portion of said aliphatic alcohol from said second mixture, thereby producing a third mixture comprising fermentable hemicellulose sugars; and
  (e) recovering said fermentable hemicellulose sugars.

2. The process of claim 1, wherein said first solution further comprises ammonia.

3. The process of claim 1, wherein said second stage includes sulfur dioxide in a concentration of from 0.05 wt % to 3 wt %.

4. The process of claim 1, wherein said second solution includes sulfur dioxide in a concentration of from 3 wt % to 9 wt %.

5. The process of claim 1, wherein said aliphatic alcohol is selected from the group consisting of methanol, ethanol, propanol, butanol, and any combinations thereof.

6. The process of claim 1, wherein step (c) is carried out at a temperature selected from 105° C. to 200° C.

7. The process of claim 1, wherein:
  said first solution consists essentially of 40 wt % ethanol, 40 wt % water, and 12 wt % sulfur dioxide;
  said second solution consists essentially of 48.5 wt % ethanol, 48.5 wt % water, and 3 wt % sulfur dioxide;
  said first stage is operated at a temperature of 140° C. for 2 hours; and
  said second stage is operated at a temperature of 140° C. for 1 hour.

8. The process of claim 1, said process further comprising separately precipitating and recovering said lignin and said lignosulfonates.

9. The process of claim 1, wherein step (d) is carried out prior to step (c).

10. The process of claim 1, said process further comprising stripping said second mixture to remove said sulfur dioxide, said aliphatic alcohol, and fermentation inhibitors.

11. The process of claim 1, said process further comprising a step of fermenting said fermentable hemicellulose sugars to produce a fermentation product.

12. The process of claim 11, wherein said fermentation product is the same as said aliphatic alcohol; said process further comprising recycling at least some of said fermentation product to said first stage.

13. The process of claim 1, wherein said first solution further comprises an additive selected from the group consisting of ammonium hydroxide, magnesium hydroxide, sodium hydroxide, urea, anthraquinone, and any combinations thereof.

14. A process for producing fermentable hemicellulose sugars from a lignocellulosic material, said process comprising:
  (a) contacting a lignocellulosic material with a first solution of an aliphatic alcohol, water, and sulfur dioxide in a first stage to produce a first mixture comprising cellulose, hemicellulose oligomers, lignin, and lignosulfonates, wherein said first amount of sulfur dioxide is in a moisture-adjusted concentration of from 12 wt % to 30 wt % in said first solution within said first stage;
  (b) removing and recovering cellulose pulp from said first mixture, to produce a second mixture comprising hemicellulose oligomers, lignin, and lignosulfonates;
  (c) contacting said second mixture with a sulfur-containing compound in a second stage, in the presence of heat, to further hydrolyze said hemicellulose oligomers into fermentable hemicellulose sugars, wherein said sulfur-containing compound is selected from the group consisting of sulfur dioxide, sulfurous acid, sulfuric acid, a lignosulfonate, and any combinations thereof, and wherein said sulfur-containing compound is in a concentration of from 0.05 wt % to 9 wt % in a second solution within said second stage;
  (d) removing at least a portion of said aliphatic alcohol from said second mixture, thereby producing a third mixture comprising fermentable hemicellulose sugars; and
  (e) recovering said fermentable hemicellulose sugars.

15. The process of claim 14, wherein said second stage includes said sulfur-containing compound in a concentration of from 0.05 wt % to 3 wt %.

16. The process of claim 14, said process further comprising separately precipitating and recovering said lignin and said lignosulfonates.

17. The process of claim 14, said process further comprising stripping said second mixture to remove said sulfur-containing compound, said aliphatic alcohol, and fermentation inhibitors.

18. The process of claim 14, said process further comprising the step of fermenting said fermentable hemicellulose sugars to produce a fermentation product.

19. The process of claim 18, wherein said fermentation product is the same as said aliphatic alcohol; said process further comprising recycling at least some of said fermentation product to said first stage.

20. A process for producing fermentable hemicellulose sugars from a lignocellulosic material, said process comprising:
  (a) contacting a lignocellulosic material with a first solution of an aliphatic alcohol, water, and sulfur dioxide in a first stage to produce a first mixture comprising cellulose, hemicellulose oligomers, and lignin, wherein said first amount of sulfur dioxide is in a moisture-adjusted concentration of from 12 wt % to 30 wt % in said first solution within said first stage;
  (b) sulfonating, in the presence of said sulfur dioxide, at least some of said lignin into lignosulfonates and lignosulfonic acids in said first stage, wherein said concentration of sulfur dioxide is selected to control the extent of lignin sulfonation;
  (c) removing and recovering cellulose pulp from said first mixture, to produce a second mixture comprising hemicellulose oligomers, lignin, lignosulfonates, and lignosulfonic acids;
  (d) introducing said second mixture into a second stage in the presence of heat, wherein said lignosulfonic acids catalyze hydrolysis of said hemicellulose oligomers into fermentable hemicellulose sugars;
  (e) removing at least a portion of said aliphatic alcohol from said second mixture, thereby producing a third mixture comprising fermentable hemicellulose sugars; and
  (f) recovering said fermentable hemicellulose sugars.

* * * * *